United States Patent

Beaty et al.

Patent Number: 5,397,269
Date of Patent: Mar. 14, 1995

[54] TORQUE LIMITING CLUTCH AND ITS USES

[75] Inventors: Keith D. Beaty, West Palm Beach; Dan P. Rogers, Royal Palm Beach, both of Fla.

[73] Assignee: Implant Innovations, Inc., West Palm Beach, Fla.

[21] Appl. No.: 67,989

[22] Filed: May 27, 1993

Related U.S. Application Data

[63] Continuation-in-part of Ser. No. 885,619, May 19, 1992.

[51] Int. Cl.$^6$ .................... F16D 7/04; F16D 7/02
[52] U.S. Cl. ........................ 464/38; 464/36; 464/39; 192/56 R
[58] Field of Search ............. 464/38, 37, 39, 35, 464/36; 433/173, 174; 192/56 R

[56] References Cited

U.S. PATENT DOCUMENTS

| | | | |
|---|---|---|---|
| 1,126,219 | 1/1915 | Hupp | 464/38 |
| 2,275,004 | 3/1942 | Behl | 464/39 |
| 2,806,366 | 9/1957 | Woestmeyer | 464/36 |
| 2,818,712 | 1/1958 | Barnes et al. | 464/36 |
| 2,927,672 | 3/1960 | Banner | 464/39 |
| 3,205,985 | 9/1985 | Pearl | 192/56 R |
| 3,942,337 | 3/1976 | Leonard et al. | 464/36 |
| 4,850,567 | 7/1989 | Ambrosi | 464/36 |

FOREIGN PATENT DOCUMENTS

| | | | |
|---|---|---|---|
| 808545 | 2/1959 | United Kingdom | 464/38 |
| 530125 | 2/1976 | U.S.S.R. | 464/39 |

*Primary Examiner*—Clifford D. Crowder
*Assistant Examiner*—Bibhu Mohanty
*Attorney, Agent, or Firm*—Alfred H. Rosen

[57] ABSTRACT

A torque limiting clutch which transmits gradually increasing torque up to a prescribed limit at which limit the clutch disengages from its load. An embodiment designed for light service use in dentistry encloses all the working parts in a housing through which torque is applied to the load, and is autoclavable, This embodiment can be attached to known dental handpieces for assembling components of dental restorations with prescribed limited torque.

20 Claims, 4 Drawing Sheets

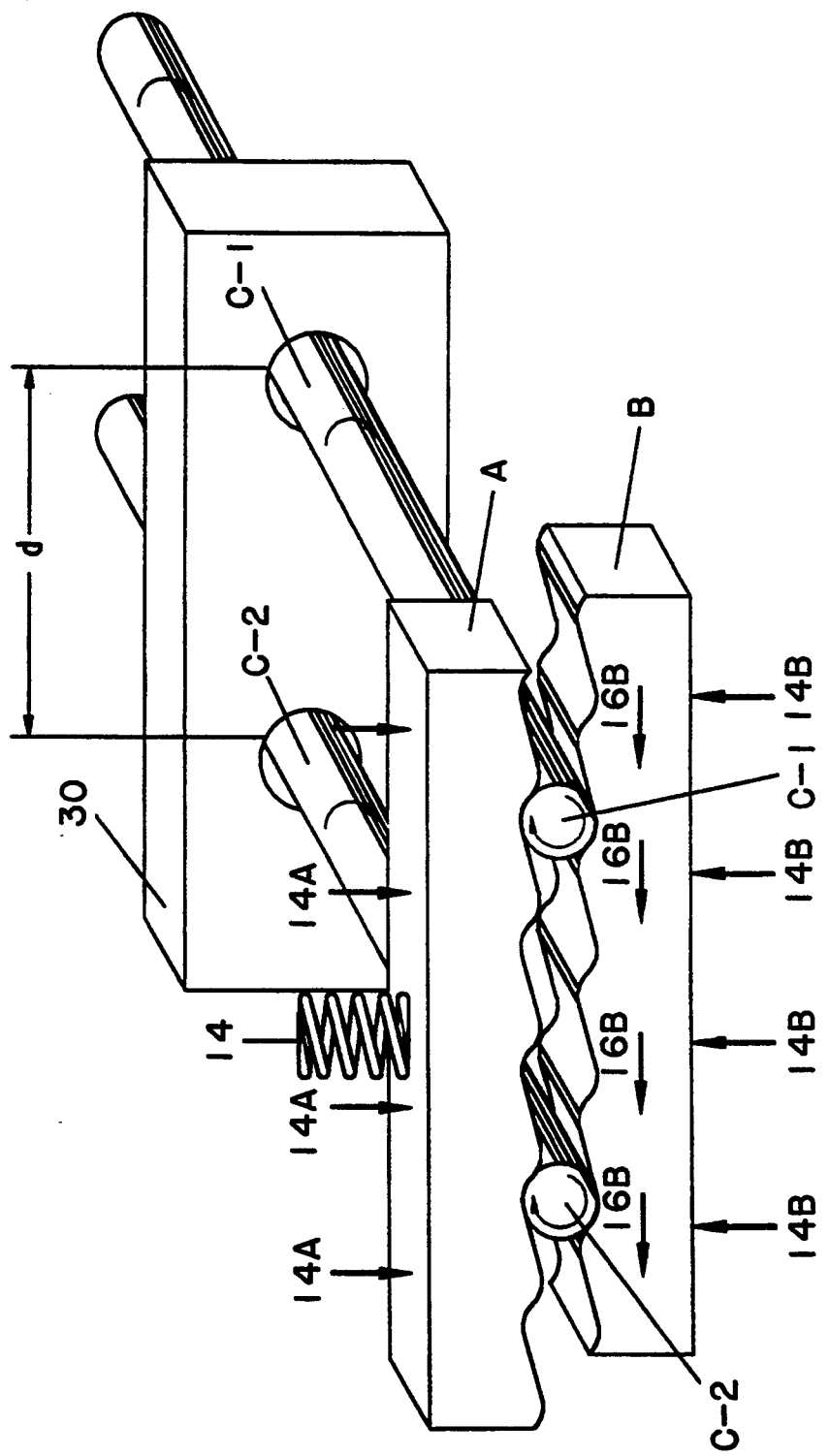

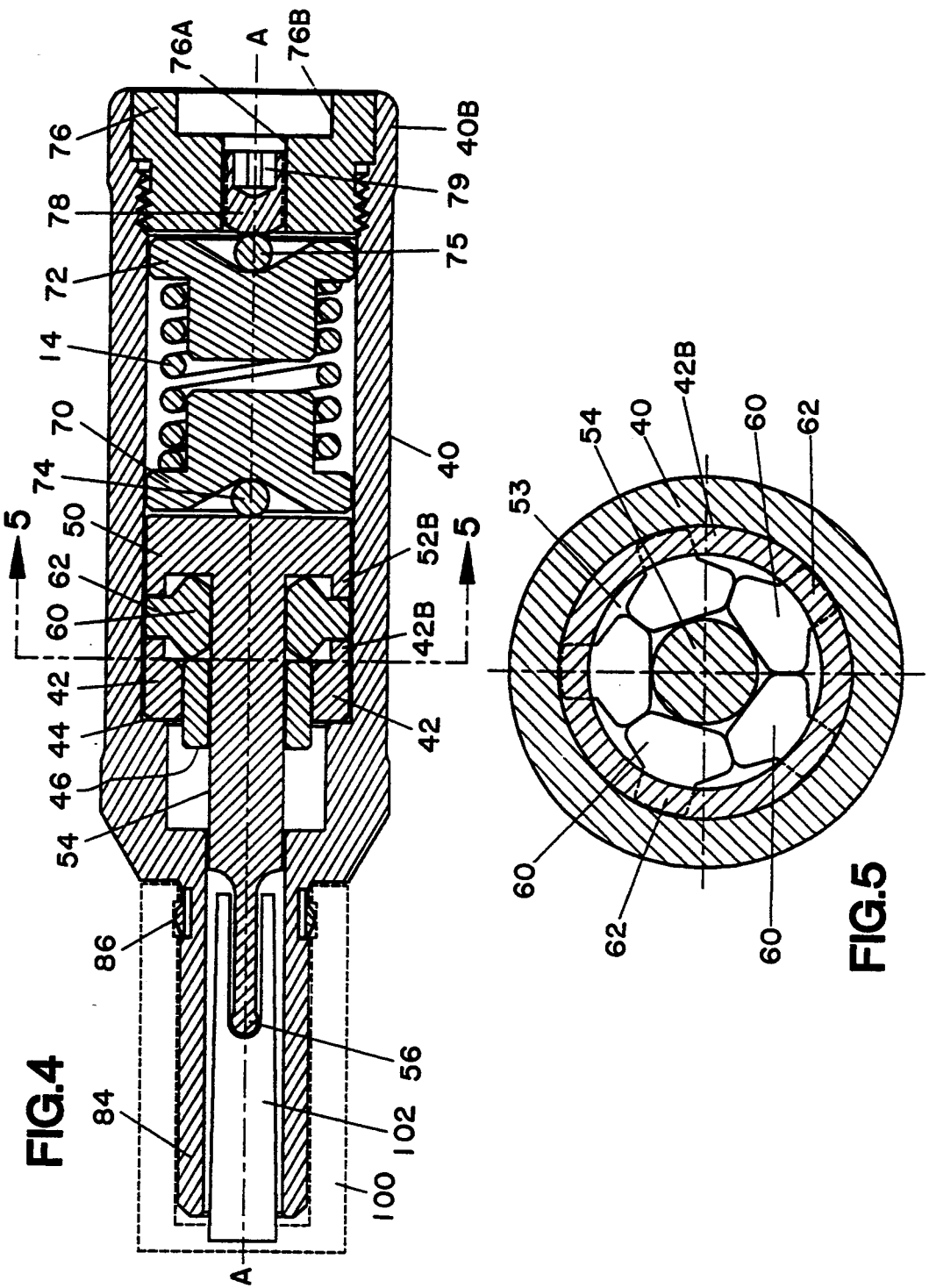

TORQUE LIMITING CLUTCH AND ITS USES

This invention relates to a new torque limiting clutch and its uses in a wide variety of applications including applications in dental and medical environments where such devices have not heretofore been suitable for use. This application is a continuation-in-part of our application Ser. No. 07/885,619 filed May 19, 1992.

BACKGROUND OF THE INVENTION

Improvements in the field of dental implantology have given restorative dentists and their partially or wholly edentulous patients the increasing option to support new artificial teeth on artificial roots. Prominent among the artificial roots that have become available is the osseointegrated dental implant fixture; commonly, this fixture takes a cylindrical form which is implantable in the patient's jawbone and has an axially located internally-threaded bore for receiving an externally threaded bolt which is used to attach to the implant fixture an artificial tooth, or an intermediate component between the fixture and the tooth. In practice one or more such bolts may be used to attach one tooth to an artificial root. The artificial tooth itself is frequently built on, or includes in its structure, a component which is designed and intended for cooperation with such a bolt. Thus, threaded bolts are important subcomponents in the structures of artificial teeth in a dental restoration supported on a dental implant fixture or fixtures.

With experience has come the realization that the bolts used in such dental restorations may have certain critical properties. The implant fixtures and the components assembled on them are made of materials chosen for suitability in dental use; presently the metal titanium is the material of choice. The bolts may suitably but not necessarily be made of gold. These are not hard metals such as steel that are commonly used in industrial structures, yet the bolts must be tightened enough so that the restored dentition will not fail in use. Attention has been given to designing and making the implant fixtures and related components to a high degree of dimensional precision and repeatability to minimize the opportunity of components to rock against each other and the implant fixture and thereby bending the attaching bolts and eventually breaking them. And, more recently, attention has been given to tightening the bolts just enough so that they will hold all the assembled parts tightly together throughout the range of forces those parts will encounter in use, but not so much that the bolts will be stretched beyond their elastic limit and break. The small sizes in which these bolts are made, as low as 1/16th of an inch, and generally not more than ⅛th of an inch in diameter at the peaks of their threads, have made this a critical and burdensome problem. To respond to the problem some tool manufacturers have provided complicated machines for controlling the torque applied to the bolts during assembly of the teeth and components on dental implant fixtures. Such machines that are currently available employ cabinets enclosing complex electronic motor control circuitry, a motor-driven handpiece for holding and driving a screwdriver bit, and a long flexible cable connecting the handpiece to the cabinet. Along with all this gadjetry is a group of settable controls on the cabinet and a handbook telling the dentist how to operate and maintain the equipment, and, of course, a correspondingly-high price.

GENERAL NATURE OF THE INVENTION

The present invention provides a torque-limiting clutch having a driving member and a driven member, each member with a confronting clutch surface having on it a periodic wave of like frequency to the other confronting surface, the two members being held with their confronting clutch surfaces facing each other, and means to apply a compressive force urging the two surfaces toward each other.

In the field of restorative dentistry incorporating dental implant fixtures and components as described above the torque forces applied to the connecting bolts are small, measured in Newton-centimeters (Ncm), and it is highly desirable that a torque-limited driver for use in driving such bolts be accurate to within approximately plus or minus one Ncm. from an original pre-set calibration of the tool. To aid in achieving this degree of precision this new clutch includes mechanical anti-friction means between the confronting clutch surfaces which requires no lubrication. This invention relates in particular to improvements in such anti-friction means, and more particularly to a new design of roller bearings used between the confronting clutch surfaces.

An embodiment of the invention suitable for use in dentistry features a unitary housing enclosing the driving member, the driven member, an assembly of the new roller bearings between the confronting wave surfaces, a unit for applying the compressive force and means to pre-set the magnitude of the compressive force in Ncm. The housing and its entire contents are without any lubricant, and are completely autoclavable. The driving member is fixed in the housing, and the driven member is held free to rotate within the housing when the pre-set torque limit is reached. The driven member has a coupling element extending from it for coupling with a tool for driving screws, bolts, nuts and the like. The housing is arranged to couple with such a tool so that rotation of the housing relative to the tool will transmit torque to the tool via the driven member. A set of torque-limited clutches, each precalibrated to a specific torque value, may be supplied for use with one tool.

Prior art showing torque-limiting clutch devices incorporating anti-friction means between the driving and driven members, known to us at the present time, is that which has been cited in our above-referenced pending application.

The invention is described in greater detail with reference to the accompanying drawings. These drawings include illustration of an embodiment of the invention that is suitable for use in dentistry, but the invention is not limited to details of that embodiment. It is intended and understood that this invention is applicable, and the scope of the appended claims extends to, all uses where it is desired to tighten, or to loosen, a screw, bolt, nut or the like with limited torque.

BRIEF DESCRIPTION OF THE DRAWINGS

FIG. 3 is an isometric view illustrating the use of roller bearings of the invention;

FIG. 4 is an axial section through a torque limiting clutch employing the new roller bearings of the invention enclosed in a housing;

FIG. 5 is a side cross-section taken on line 5—5 in FIG. 4;

DETAILED DESCRIPTION OF THE DRAWINGS

Figure 1:
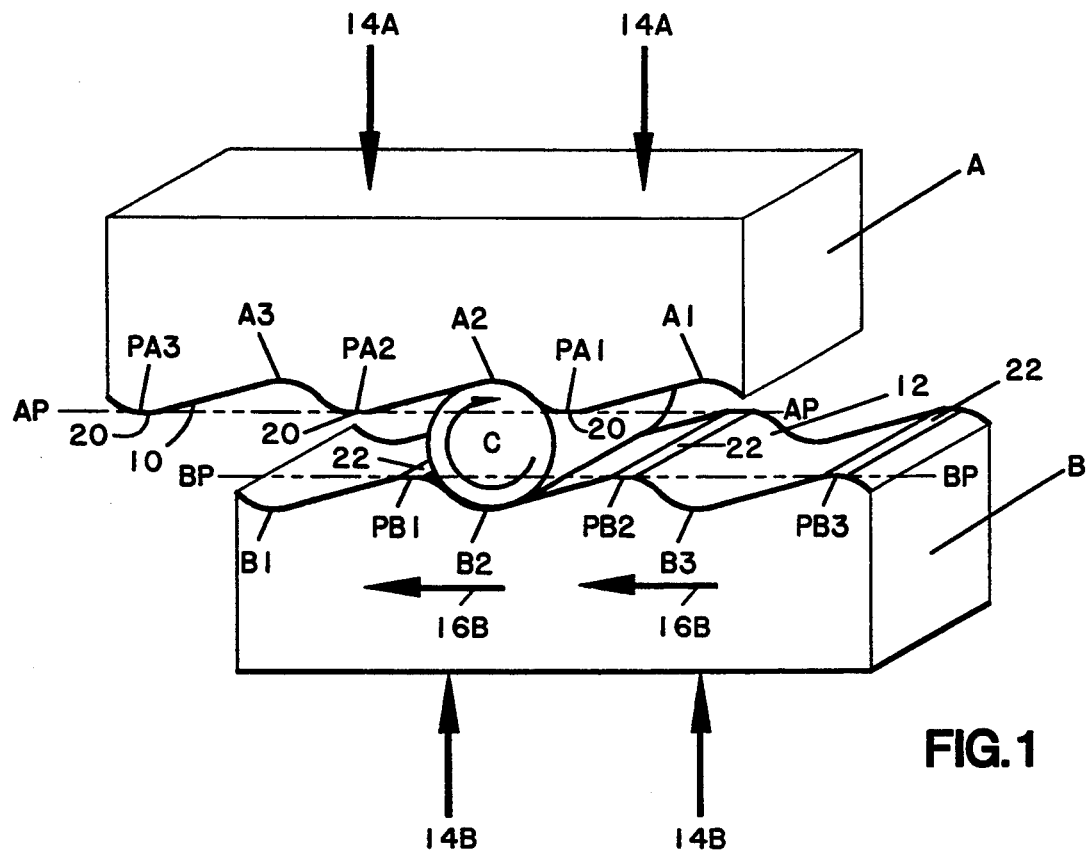
FIG. 1 is an isometric view illustrating basic principles of the invention.

In FIG. 1 a driven member A and a driving member B have confronting clutch surfaces 10 and 12, respectively, confronting each other, with an anti-friction roller C between them. A compressive force urging the two members together is represented by arrows 14A and 14B. A torque force applied to the driving member B in the direction of arrows 16B will move the driven member A in the same direction if the driven member does not resist, owing to the periodic wave-form shape of each surface 10 and 12. Three cycles of the wave form on each surface are shown; they are alike in frequency, period, and wave pattern, so that in the absence of the roller C the two confronting surfaces could nest together substantially uniformly. For convenience, the dwells in the wave form of the driving member B are labelled B1, B2 and B3, and the peaks are labelled PB1, PB2 and PB3. Likewise, on the driven member A the dwells are labelled A1, A2 and A3, while the peaks are labelled PA1, PA2 and PA3. FIG. 1 shows the torque limiting clutch in its rest position, as when no torque force is applied; in this position the roller C is nested between two dwells A2 and B2, and the two members A and B are as close to each other as they can be.

For purposes to be presently explained, each wave surface has a flat portion, 20 in driven member A and 22 in driving member B, at each peak. The flat portions 20 are in a common plane AP-AP, and the flat positions 22 are in a second common plane BP-BP, and these two planes are substantially parallel to each other.

The individual wave forms, as shown in this embodiment of the invention, are asymmetrical. Thus, referring to a single wave form B3 near the right-hand end of the driving member (as seen in the drawing), the segment of the wave form between its dwell B3 and its peak PB3 has a relatively gradual slope, whereas the remaining sector between the dwell B3 and the next succeeding peak PB2 has a shorter and relatively steeper slope. With this structure incorporated in its design, the torque-limiting clutch of the invention can have one value of torque limit when driven in one direction, and a different value of torque limit when driven in the opposite direction.

Figure 2:
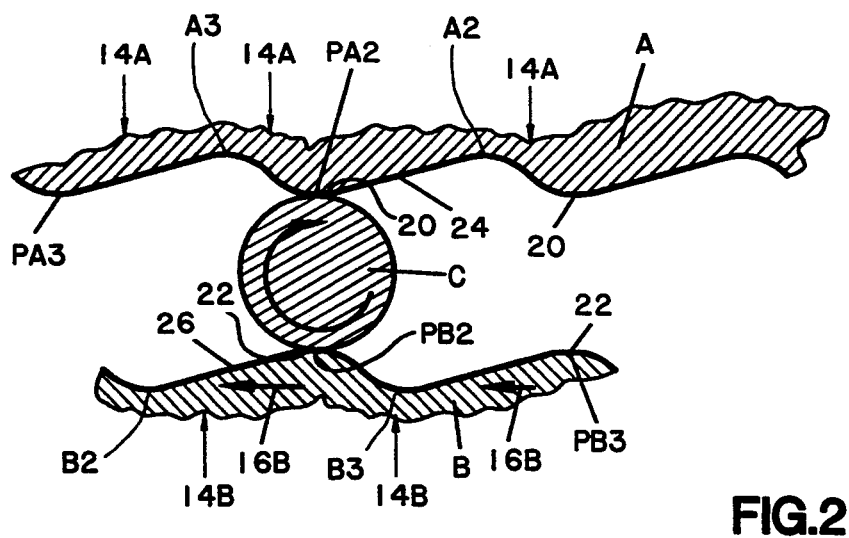
FIG. 2 is a sectional view illustrating the torque-release performance of the invention.

FIG. 2 illustrates the configuration of the driving and driven members B and A, respectively, at the moment of torque release, when the driving member loses driving connection with the driven member. Assume that the torque force represented by the arrows 16B has been resisted by the driven member A against the compressive force represented by arrows 14A and 14B, the driving member B slipping past the driven member A forces the roller C to roll out of the dwells B2 and A2 and to roll "up" the slope 24 leading to the following wave peak PA2, and "up" the slope 26 leading to the following wave peak PB2, until if resistance of the driven member A exceeds the pre-set torque limit the roller C is brought to a position between two confronting flat portions 20 and 22. This is the position of torque limit, in which the driving member B can no longer drive the driven member A. Following this event, the driving member B is decoupled from the driven member A and continues to move in the direction of arrows 16B until the roller C is forced ("falls") into the next pair of dwells A3 and B3 under the compressive force 14A and 14B, at which point the driven member A is again coupled to the driving member B, and driving torque is regained. When torque is lost the distance between the two members reaches a maximum, and that distance reaches a minimum when torque is regained.

The single anti-friction roller C shown in FIGS. 1 and 2 is sufficient to illustrate how the invention uses roller bearings. In practice it is preferred to use a plurality of anti-friction rollers, for example one roller for every two cycles of the confronting wave configurations. FIG. 3 schematically illustrates this version of the invention. To simplify the illustration only two rollers C-1 and C-2 are shown, spaced two wavelengths apart between the driving member B and the driven member A. A coil spring 14 is illustrated as a means to apply compressive force represented by the arrows 14A. In the illustration under discussion, the rollers are loosely held in a cage 30 which permits them to turn around their respective axes but holds the spatial distance "d" between their axes fixed at two wavelengths. It will be understood that additional rollers, not illustrated, can be added, one for each wavelength, and that the illustrated cage can provide a socket for each of them. According to the present invention, the cage can be dispensed with, as will be described following.

Figure 6:
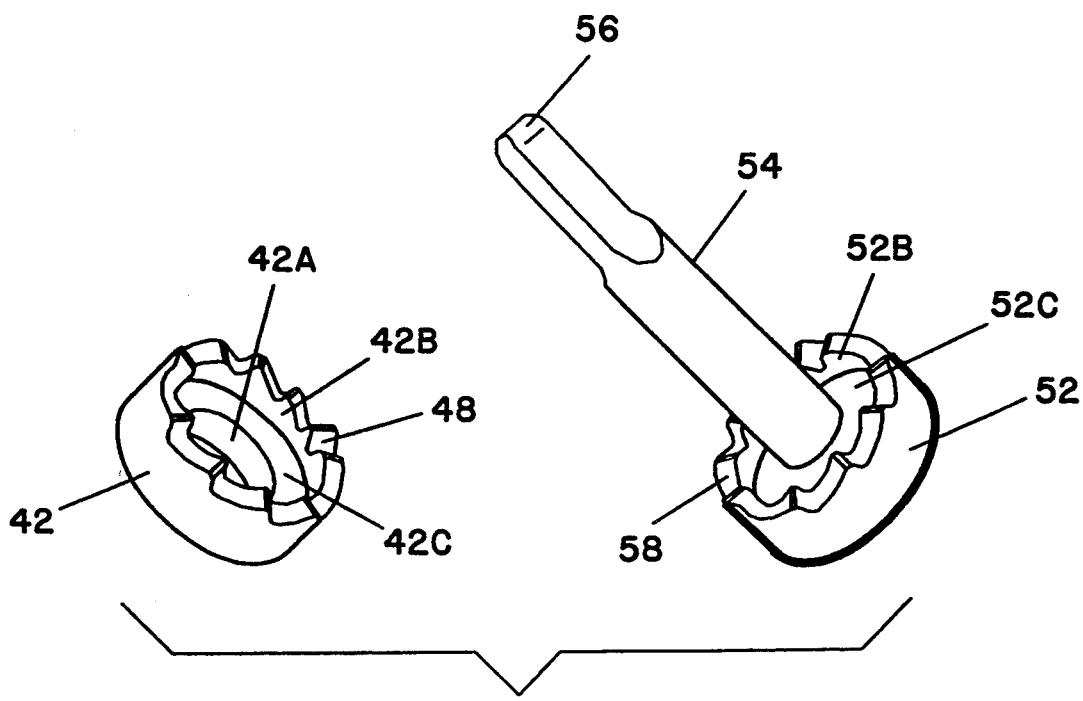
FIG. 6 is an exploded view showing certain components of FIG. 4 in detail.

A practical embodiment of the invention, which has been devised for use in dentistry, and which uses improved roller bearings of the invention, is illustrated in FIGS. 4. A hollow round housing 40 encloses all the parts of the clutch mechanism. The driving member 42 is annular in form and it is fixed in the housing where it rests on a shelf 44. The driving member has a main annular body portion 42A in which a sleeve bearing 46 is fitted, and a thinner annular coronal portion 42B having the same outer diameter as the main body portion 42A and forming an interior shelf 42C with the main body portion. The wave configuration of the driving member 42 is carried on the annular coronal surface 48 (shown in FIG. 6). The driven member 50 has a main body 52 of cylindrical outer shape dimensioned to fit within the housing 40, and bearing a coronal portion 52B which confronts the coronal portion 42B of the driving member. The wave configuration of the driven member is carried on the annular surface 58 of the driven member. A drive shaft 54 having a coupling element 56 is axially integral with, or affixed to, the driven member, for driving a tool through the torque-limiting clutch. A plurality of anti-friction rollers 62 are held in place between the confronting coronal surfaces 48 and 58.

In prior art designs using a cage to hold anti-friction rollers in radial positions there is a tendency of the rollers to shift or move radially outward in the cage, and to rub endwise on the inner surface of the clutch housing 40. This action, when it occurs, can cause undue wear and degradation of the accuracy of torque-limit adjustments. In the present invention the roller bearings are self-caging and are restrained from shifting radially outward. Each roller has a roller section 62 between the clutch faces 48 and 58, and an expanded somewhat bulbous caging section 60 which largely fills the annular space 53 (shown in FIG. 5) between the coronal portions 42B and 52B of the clutch members and the torque-output shaft 54. As appears in FIG. 5 the caging sections 60 are shaped and sized so that they are restrained from wobbling in a circumferential direction in that space, thereby fulfilling the function of a roller bearing cage. At the same time the caging sections, being too large to move radially outward between the coronal portions 42B and 52B are confined in their annular space, in consequence of which the roller sections 62 cannot migrate radially outward toward the inner wall of the housing 40.

Figure 7:
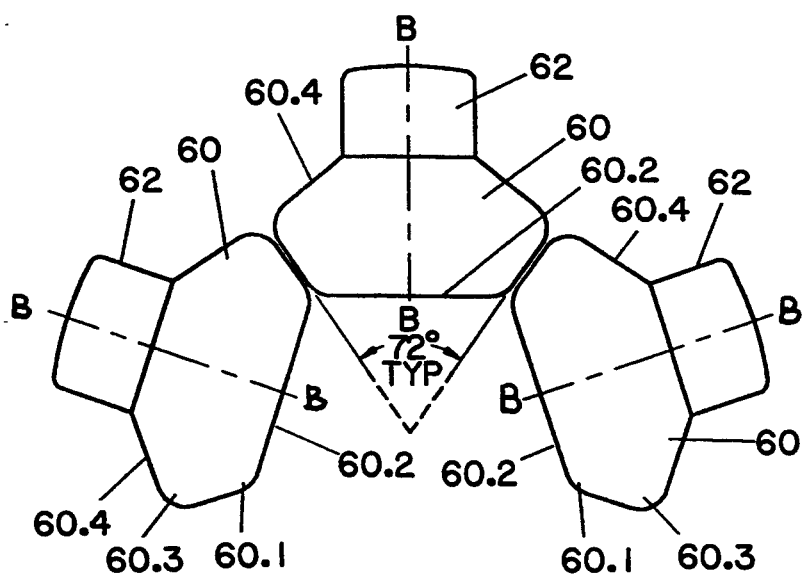
FIG. 7 is an enlarged view of the new bearings.

FIG. 7 is an enlarged schematic representation of three of the roller bearings shown in FIG. 5. In each roller bearing the roller section 62 is coaxial with the caging section 60, on a common axis B—B. Each roller section 62 is substantially cylindrical, and each caging section is substantially conical with an included angle that is 360 degrees divided by "n" where "n" is the number of roller bearings used. In this instance, where five roller bearings are used, the included angle is 72 degrees, as shown in FIG. 7. Each caging section is truncated at its narrower end in a flat surface 60.2 that is substantially normal to the relevant axis B—B. Each caging section is truncated at its wider end 60.3 in a convex surface 60.4 that is contoured to fit within the annular space 53. The flat surfaces 60.2 can make linear tangential contact with the torque output shaft 54. The roller bearing axes B—B are substantially radially normal to the axis A—A of the housing 40.

Compressive force to hold the driving and driven members together is applied by a spring 14 that is fitted between two end blocks 70 and 72, which as here illustrated are identical, each having a depression in its outer surface for receiving an anti-friction ball bearing 74 and 75, respectively. A closure block 76 is fitted into the remote end 40B of the housing 40, compressing the spring 14 on the shelf 44 with the clutch components between them. This closure block may be used to apply an initial compressive force to the driving and driven members of the clutch. The closure block 76 has an internally-threaded bore 76A into which an adjusting screw 78 is threaded. This adjusting screw is advanced onto the ball bearing 75 in the spring block 72 confronting the closure block, for adjusting the magnitude of the compressive force of the spring 14. A wrench socket 79 is provided in the free end of the adjusting screw for this purpose. In assembling the parts of the clutch the closure block may be used to apply an initial compressive force to the spring 14, and the spring may be used to increase that force by a desired increment, or the closure block may leave the spring unloaded and the screw may be used to apply and adjust the entire compressive force. In either case, the screw is used to adjust the torque limit of the clutch. After this adjustment has been made, a cover disc (not shown) is fitted into a recess 76B surrounding the bore 76A to cover the screw 78 and prevent tampering with it. The value of the torque limit set into the clutch may be entered on this disc. For convenience of dentists using it, values such a 10 Ncm., 20 Ncm., and 32 Ncm., are presently in use.

As appears in FIGS. 4 the shaft 54 of the driven member 50 fits coaxially within the circular space surrounded by the caging sections 60 and the sleeve bearing 46, within which it is free to rotate. When the housing 40 is turned on the common axis A—A of these parts the driving member 42 turns with it and, by its clutch action turns the driven member 50 against a resisting load that may be coupled to the coupling element 56.

The housing has a tubular extension 84 surrounding the coupling element, and bears an annular resilient latch 86 around it at the junction with the housing, for coupling to a standard dental hand tool, represented generally by tool housing 100 and drive shaft 102.

The parts of the torque-limiting clutch show in FIGS. 4 are all made of materials that can be sterilized for dental or medical use, such as stainless steel. The clutch shown in this embodiment of the invention can be autoclaved. It is rugged, reliable, accurate and suitable for dental and medical uses. It is small, portable, and requires no external source of power. The spring 14 may desirably be a helical spring made of type 302 stainless steel which is stable in compression/tension up to a maximum temperature of 550° F. The clutch is intended to be autoclavable at a temperature up to 280° F., so that autoclaving will not affect its accuracy.

We claim:

1. A slipping clutch comprising a rotatable driving member having a face with first wave-like contours thereon, a rotatable driven member having a face with second wave-like contours thereon similar to said first contours, a plurality of substantially cylindrical self-caging anti-friction rollers disposed between said faces, one of said members being axially movable in either direction, self-cage means having a portion of larger diameter than said roller endwise integral with each of said rollers for locating said rollers between said first and second wavelike contours, and force means for applying a predetermined force for urging said one member toward the other member to maintain said rollers in contact with said faces.

2. A slipping clutch as set forth in claim 1, said force means being adjustable whereby the magnitude of said predetermined force can be varied.

3. A clutch according to claim 1 in which the cage means of each of said rollers has a tapering diameter that is substantially everywhere greater that the diameter of its roller member.

4. A slipping clutch comprising rotatable driving means, a driving member mounted to rotate with said driving means, said driving member having an annular face with first contours thereon of a predetermined wavelike pattern, a driven member rotatably mounted on said driving means and adapted to impart torque to a load, said driven member having an annular face with second contours thereon similar to those on said driving member, a substantially annular cage space defined between said members, a plurality of spaced rollers each having a self-cage member located in said cage space and a roller member extending out of said cage space between said faces, means for applying a predetermined force urging the driving and driven members together to maintain the rollers in contact with said faces, said cage member of each roller member maintaining said roller member in a predetermined radial location, relative to the axis of rotation of said driving means.

5. A clutch according to claim 4 in which each of said rollers is a unitary body symmetrical around a roller axis of rotation and having its roller member extending on said roller axis from its cage member, and each of said cage members is shaped as a cone symmetrical around said roller axis and having an included angle which is substantially 360 degrees divided by "n" where "n" is the number of said plurality whereby said cage members of said plurality can substantially fill said cage space when said cage members are arrayed in said cage space holding said roller members each in said predetermined radial location.

6. A clutch according to claim 5 in which each of said cage members is truncated to a substantially flat surface at its narrower end.

7. A clutch according to claim 6 in which said flat surfaces make respective line contacts with the locus of a cylinder that defines the smaller boundary of said cage space.

8. A clutch according to claim 5 in which each of said cage members is truncated to a substantially convex surface at its wider end.

9. A clutch according to claim 8 in which said convex surfaces fit within the larger boundary of said cage space.

10. A clutch according to claim 5 in which each of said cage members is truncated to a substantially flat surface at its narrower end and to a substantially convex surface at its wider end, for fitting said cage members within the boundaries of said cage space.

11. A clutch according to claim 5 in which said roller members extend radially out of said cage space.

12. A clutch according to claim 10 in which said roller members extend radially out of said cage space.

13. A clutch according to claim 4 in which the cage member of each of said rollers has a diameter that is greater than the diameter of its roller member.

14. A slipping clutch comprising a rotatable driving member having a face with wavelike contours thereon, a rotatable driven member having a face with wavelike contours thereon similar to the contours on the driving member face, a bore through a first of said members, said bore aligned on the axis of rotation of said first member, support means for holding said members with said faces confronting each other, said first member being fixed in said support means, the second of said members having an elongated torque output shaft fixed at one end to said face of said second member on its axis of rotation, said second member being axially movable in either direction in said support means with said shaft extending from said second member out of said support means through said bore, anti-friction means comprising radially-oriented rollers between said faces, said rollers having integral retainer means for restraining said rollers from migrating radially outward relative to said faces, and force means resident in said support means for applying a predetermined force for urging said second member toward face-to-face contact with said first member.

15. A clutch according to claim 14 in which each of said faces has on it a periodic wave of like frequency to the other in which the wave pattern of each cycle has an up-slope rising gradually from its dwell to a peak followed by a return slope falling to the dwell at the beginning of the next-following cycle.

16. A clutch according to claim 15 in which each of said slopes is substantially linear.

17. A clutch according to claim 14 in which said support means is a support housing enclosing said members and said force means, said support housing having an opening in register with said bore for passage of said torque output shaft out of said support housing.

18. A clutch according to claim 17 in which said support housing has a tubular extension extending substantially from the periphery of said opening and surrounding said torque output shaft.

19. In combination, a clutch according to claim 18 and a tool having an elongated tubular tool housing and a drive shaft in said tool housing, coupling means for connecting said tubular extension end-to-end on a common axis with said tool housing with freedom to rotate said support housing around said axis relative to said tool housing.

20. A clutch according to claim 14 in which said means of each of said rollers is a figure of revolution having a diameter that is greater than the diameter of its roller.

* * * * *